United States Patent
Chatellier et al.

(10) Patent No.: US 7,421,901 B2
(45) Date of Patent: Sep. 9, 2008

(54) METHOD OF USING ULTRASOUND TO INSPECT A PART IN IMMERSION

(75) Inventors: Jean-Yves Francois Roger Chatellier, Arcueil (FR); Richard Michael Coulette, Gentilly (FR)

(73) Assignee: Snecma, Paris (FR)

( * ) Notice: Subject to any disclaimer, the term of this patent is extended or adjusted under 35 U.S.C. 154(b) by 301 days.

(21) Appl. No.: 11/335,639

(22) Filed: Jan. 20, 2006

(65) Prior Publication Data

US 2006/0162457 A1 Jul. 27, 2006

(30) Foreign Application Priority Data

Jan. 27, 2005 (FR) ................................. 05 00835

(51) Int. Cl.
*G01N 29/06* (2006.01)
*G01N 29/26* (2006.01)
*G01N 29/30* (2006.01)
(52) U.S. Cl. ............................ 73/621; 73/634; 73/644
(58) Field of Classification Search .................. 73/620, 73/621, 634, 644
See application file for complete search history.

(56) References Cited

U.S. PATENT DOCUMENTS

| 5,005,420 A * | 4/1991 | Miyajima ..................... 73/629 |
| 5,497,662 A * | 3/1996 | Dykes .......................... 73/634 |
| 5,565,627 A | 10/1996 | Dorr |
| 2006/0048576 A1* | 3/2006 | Kiuchi et al. ................. 73/593 |
| 2006/0179947 A1* | 8/2006 | Chatellier et al. ............. 73/579 |

FOREIGN PATENT DOCUMENTS

JP     62-85860     4/1987

OTHER PUBLICATIONS

J. Krautkraemer, et al., "Ultrasonic Testing of Materials", Springer-Verlag, Third, revised Edition, XP-002352087, 1983, pp. 228-241 and pp. 307-311.

* cited by examiner

*Primary Examiner*—Hezron E. Williams
*Assistant Examiner*—Rose M Miller
(74) *Attorney, Agent, or Firm*—Oblon, Spivak, McClelland, Maier & Neustadt, P.C.

(57) ABSTRACT

A method of inspecting a part in immersion using a focused beam of ultrasound waves oriented perpendicularly to the surface of the part, the method including, when the axis of the focused beam is close to an edge of the part, tilting the axis towards the edge relative to the normal to the surface of the part in order to eliminate the lateral shadow zone over all or substantially all of the depth of the part.

8 Claims, 3 Drawing Sheets

METHOD OF USING ULTRASOUND TO INSPECT A PART IN IMMERSION

The present invention relates to a method of inspecting a part in immersion by means of a focused ultrasound wave beam in order to detect defects in the part such as, for example, bubbles, inclusions, etc.

BACKGROUND OF THE INVENTION

This technique is implemented in a vessel filled with an acoustic coupling liquid such as water, using an ultrasound transducer that is immersed in the water and that is pointed towards the part to be inspected perpendicularly to a surface thereof, the transducer being separated from the surface of the part by a depth of water referred to as the "water column".

The transducer emits a focused beam of ultrasound waves, some of which are reflected at the surface of the part, while the remainder are transmitted to the inside of the part, the transmitted ultrasound waves possibly encountering an internal defect capable of reflecting them on their path within the part. The echoes coming from these reflections are picked up by the transducer, and the amplitudes of the echoes represent the magnitudes of the detected defects.

In practice, ultrasound inspection of a part involves relative displacement between the part and the transducer or a series of transducers serving to scan the part by one or more focused ultrasound beams.

When a focused ultrasound beam comes progressively closer to the edge of the part, an ever-increasing fraction of the beam passes beyond the edge of the part such that a fraction of the energy of the focused beam is emitted outside the part and cannot be reflected by a defect in that portion of the part which is covered by the focused beam.

Consequently, a defect that is detected in the form of an echo will be detected with amplitude that becomes ever-smaller on the focused beam getting closer to the edge of the part, with said amplitude becoming zero when the focused beam no longer encounters the part.

The fraction of the part in which this phenomenon leads to a decrease in the amplitude of the echo produced by reflection of the focused beam on a defect, constitutes a zone that cannot be inspected by known methods, and it is referred to as a "shadow" zone or as a "lateral dead" zone of the part.

The prior art technique does not enable this lateral dead zone to be eliminated over the full depth of the part, and, by precaution, it is necessary to give it some over-dimensioned potential value, e.g. 12 millimeters (mm), even though it is in fact smaller than that, e.g. half as wide, and that corresponds to a relatively large loss of material.

OBJECTS AND SUMMARY OF THE INVENTION

A particular object of the invention is to use ultrasound to inspect an immersed part by eliminating the lateral shadow zones, where such inspection is simple, effective, and inexpensive.

To this end, the invention provides a method of using ultrasound to inspect a part in immersion, the method making use of a transducer emitting a focused ultrasound wave beam and picking up the echoes produced by the focused beam being reflected on any defects in said part, the axis of the emitted focused beam being perpendicular to the surface of the part, the method consisting in using a multi-element annular ultrasound transducer associated with electronic focusing means, and when the axis of the focused beam is close to an edge of the part and is passing into a corresponding shadow zone that might mask a defect present in said zone, at least to some extent, in tilting the axis of the focused beam towards the edge of the part relative to the normal to the surface of the part, by an angle that is small enough to avoid modifying the amplitude of the wave reflected by the defect, and large enough to eliminate the lateral shadow zone over all or substantially all of the depth of the part.

The method of the invention makes it possible to detect a defect close to an edge of the part and situated in a lateral shadow zone, in the same manner as for a defect lying outside the shadow zone. The signal reflected by the defect is returned towards the transducer in the direction of incidence, such that the amplitude of the echo picked up by the transducer is substantially equal to the amplitude of the echo that would be reflected by an identical defect present at the same depth, but outside the shadow zone and detected by a beam emitted by the transducer perpendicularly to the surface of the part. It is thus possible to inspect the entire volume of the part in accurate manner.

According to another characteristic of the invention, the method consists initially in using calibration parts to measure first values for said angle beyond which the shadow zone is eliminated at different depths in the part, and in selecting for inspection purposes, an angle that is not less than or that is slightly greater than the largest of the first measured values.

The method also consists in measuring, on a calibration part, a second angle of inclination, beyond which the amplitude of the wave reflected by a defect begins to decrease with increasing angle, and in selecting for inspection purposes an angle of inclination for the axis of the focused beam that lies between the maximum of the first measured values, and said second measured value.

In practice, the angle of inclination of the incident focused beam relative to the normal to the surface of the part is about 3°, when it is desired to eliminate the shadow zone in a part made of titanium.

The method also consists in determining beforehand the extent of the shadow zone from the edge of the part, thus making it possible to inspect a major fraction of said part with a focused ultrasound beam that is oriented perpendicularly to the surface of the part, and to tilt the focused beam only on penetrating into the shadow zone.

BRIEF DESCRIPTION OF THE DRAWINGS

Other characteristics, details, and advantages of the invention appear on reading the following description made by way of non-limiting example with reference to the accompanying drawings, in which.

MORE DETAILED DESCRIPTION

Figure 1:
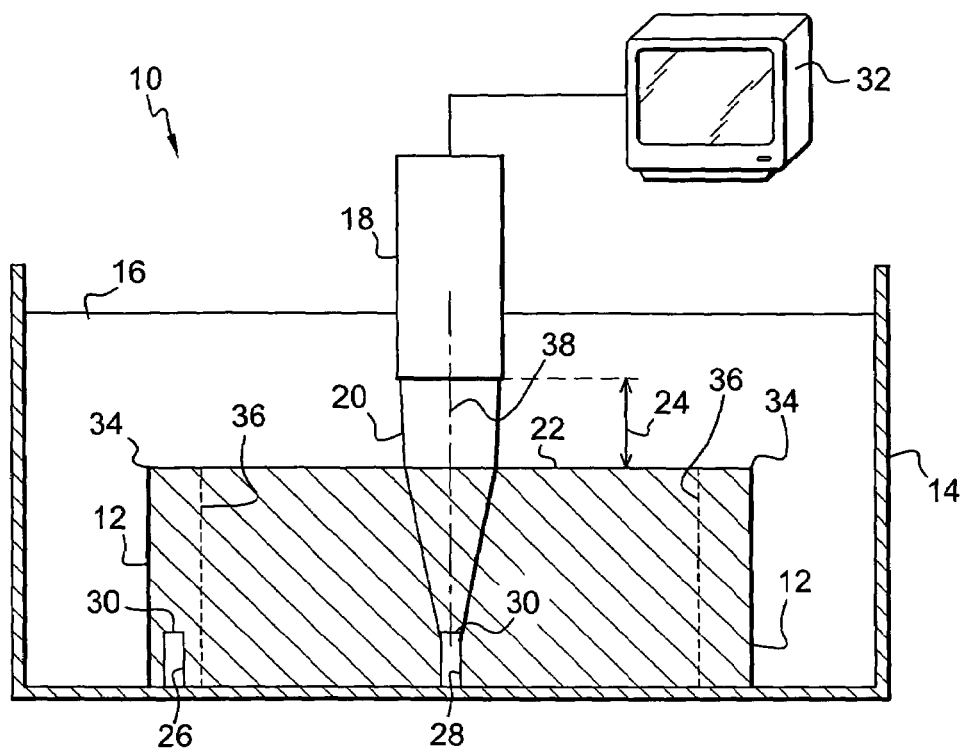
FIG. 1 is a diagrammatic section view of a device for ultrasound inspection of an immersed part.

FIG. 1 is a diagram of a device 10 for ultrasound inspection of an immersed part 12, the device comprising a vessel 14 filled with water 16 in which the part 12 for inspection is immersed together with an ultrasound transducer 18 generating a focused beam 20 of ultrasound waves oriented perpendicularly to a surface 22 of the part 12, the transducer 18 being separated from said surface 22 of the part by a depth of water referred to as the "water column" 24.

The transducer 18 is a multi-element ultrasound transducer associated with electronic focusing means and connected to control means, such as a microcomputer.

Some of the emitted ultrasound waves are reflected at the surface 22 of the part while the remainder are transmitted into the inside of the part, the ultrasound waves that are transmitted inside the part 12 possibly encountering a defect capable of reflecting them along their path. By way of example, a defect might be a bubble, an inclusion, etc., and is represented in calibration parts by a hole 26, 28 having an end wall 30 that is flat and that is situated at the end of the hole that is nearer to the surface 22 of the part, the hole opening out into the bottom surface of the part 12.

The incident waves striking the ends of the holes or on defects in parts are reflected towards the multi-element transducer in the direction of incidence, even when said direction is not perpendicular to the surface of the part. The echoes due to the ultrasound waves being reflected on the ends 30 of the holes are picked up by the transducer 18 and are recorded and displayed on display means 32 for displaying their amplitude, such as an oscilloscope connected to the transducer 18.

When using ultrasound to inspect the part 12, the transducer 18 is moved over the surface of the part 22 parallel thereto and at a predetermined value for the water column 24.

When the focused ultrasound beam 20 is close to an edge 34 of the part and passes into a corresponding shadow zone, diagrammatically outlined in FIG. 1 by dashed lines 36, the amplitude of the wave reflected by a defect 26 present in said zone is much smaller than the amplitude of an identical defect 28, but present at the same depth outside said zone 36. As a result, it is difficult to locate and evaluate the magnitude of defects that are present in the zone 36.

The method of the invention makes it possible to inspect an entire part 12 with accuracy by means of a focused ultrasound wave beam, by eliminating the lateral shadow zones of the part.

When the axis 38 of the focused beam comes to close to an edge 34 of the part and passes into a corresponding shadow zone 36 that might at least partially mask a defect 26 present in said zone 36, the method consists in tilting the axis 38 of the focused beam towards the edge 34 of the part relative to the normal to the surface 22 of the part, through an angle that is small enough to avoid changing the amplitude of the wave reflected by the defect 26, but large enough to eliminate the lateral shadow zone 36 over all, or substantially all, of the depth of the part 12.

Figure 2:
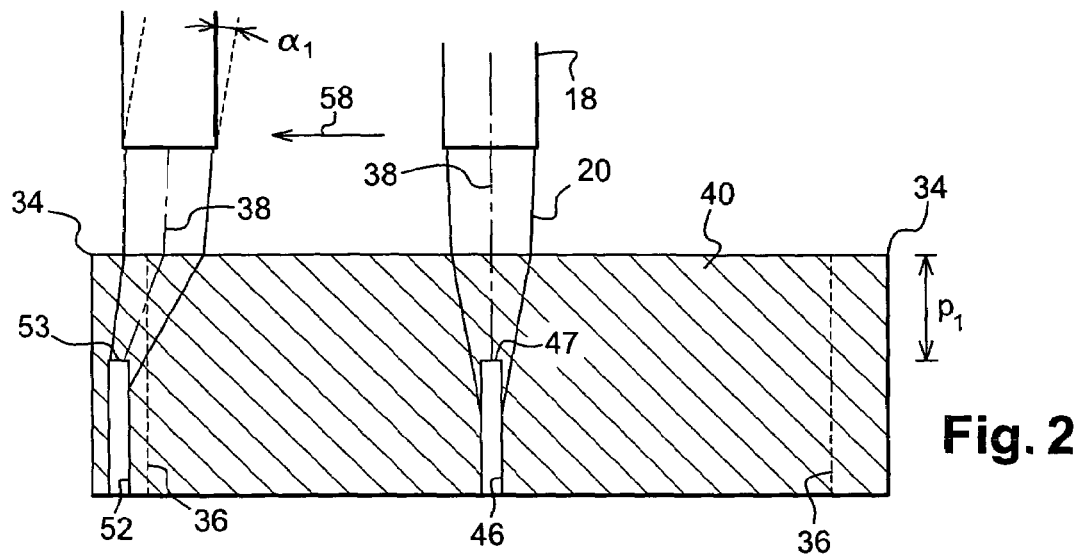
FIGS. 2 to 4 are diagrammatic section views of calibration parts showing a step in the method of the invention for inspecting a part by ultrasound.
Figure 3:
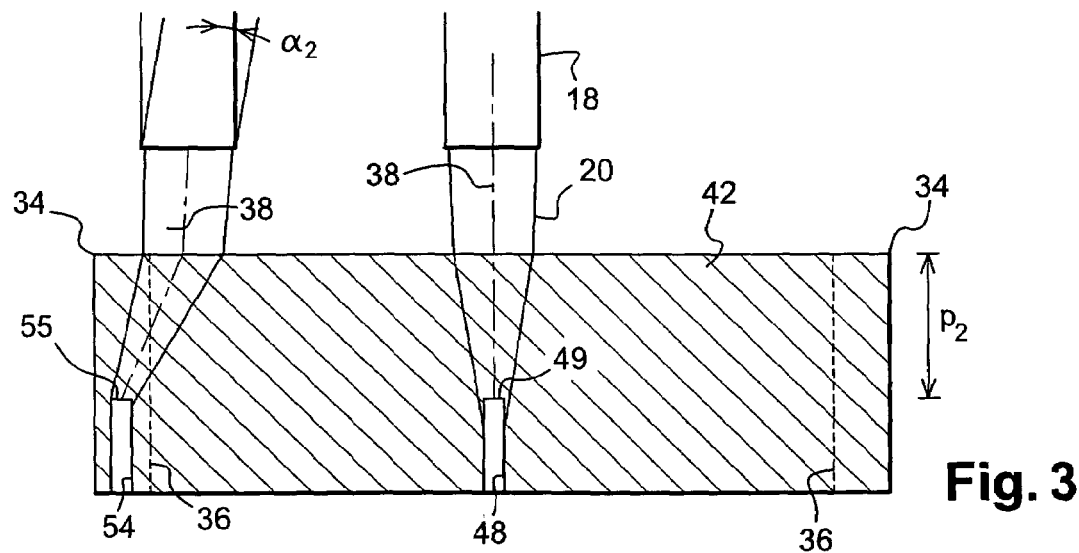
Figure 4:
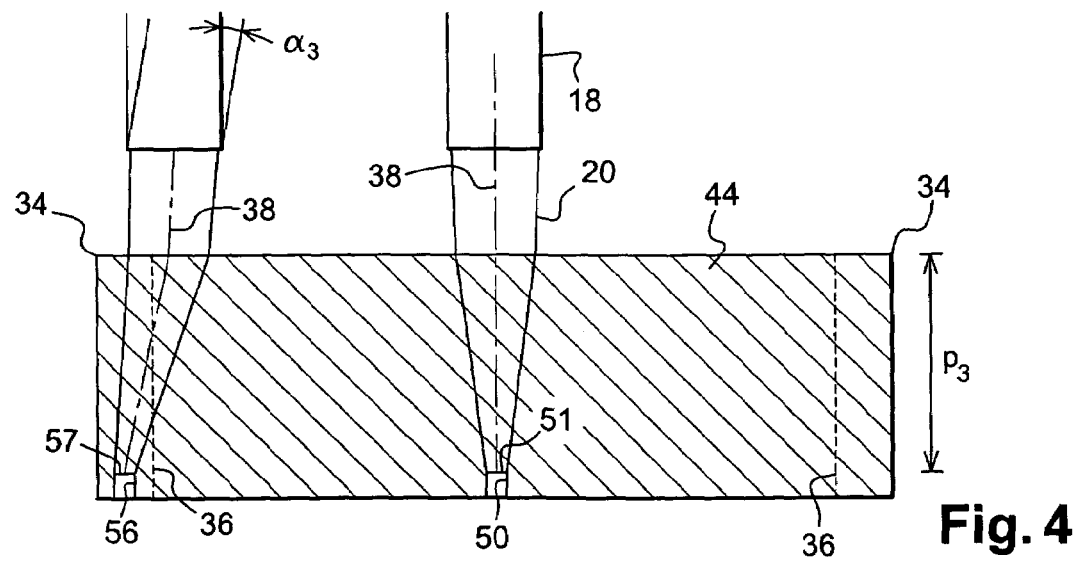

The values for this angle are determined using calibration parts, as shown in FIGS. 2 to 4.

In FIG. 2, a calibration part 40 has a hole 46 with a flat end 47 that is far enough away from the edges 34 of the part to lie outside the corresponding lateral shadow zones, and another hole 52 that is identical, having a flat end 53, is sufficiently close to an edge 34 of the part for it to be masked by the corresponding shadow zone 36, with the flat ends 47 and 53 of the holes 46 and 52 being situated at a depth $p_1$ from the surface of the part 40.

The shadow zone 36 may be set arbitrarily, e.g. as being 12 mm, or it may be determined by using a technique that is described in detail below.

The transducer 18 is spaced away from the surface of the part by a water column of predetermined value, and the axis 38 of the focused ultrasound beam is oriented perpendicularly to the surface of the part 40 and is in alignment with the hole 46 in the part in order to measure the maximum amplitude of the echo produced by the reflection of the focused beam on the flat end 47 of the hole. In practice, the means 32 are adjusted so as to display this amplitude at 80% of the height of the screen.

The transducer 18 is then moved in translation over the part 40 in the direction of arrow 58 towards the hole 52 in the part and parallel to the surface of the part, until the focused ultrasound beam 20 comes into the vicinity of the axis of the hole 52.

The method then consists in tilting the axis 38 of the focused beam towards the edge 34 of the part relative to the normal to the surface of the part through an angle $\alpha_i$ for which the amplitude of the wave reflected on the flat end 53 of the hole returns to a maximum, i.e. is substantially equal to the previously measured amplitude of the wave reflected on the flat end 47 of the hole 46. For this angle of inclination, the shadow zone is eliminated at the depth of the flat end 53 of the hole.

In practice, the angle of inclination from which the shadow zone 36 is eliminated at this depth is determined by tilting the axis 38 of the focused beam progressively towards the edge 34 of the part while using the means 32 to display the variation in the amplitude of the wave reflected on the end 53 of the hole.

FIGS. 3 and 4 show that the same procedure as that described above is performed on calibration parts 42, 44 having holes 48 & 54 and 50 & 56 with respective flat ends 49 & 55 and 51 & 57 at depths $p_2$ and $p_3$ that are different from each other and from the depth $p_1$.

The angles of inclination $\alpha_1$, $\alpha_2$, and $\alpha_3$ of the axis 38 of the focused beam are determined beyond which the dead zone 36 disappears and the amplitudes of the waves reflected on the flat ends 53, 55, 57 of the holes 52, 54, and 56 reach maximum values, and these determinations are carried out again on other flat-ended holes situated at increasing depths within the part.

Figure 5:
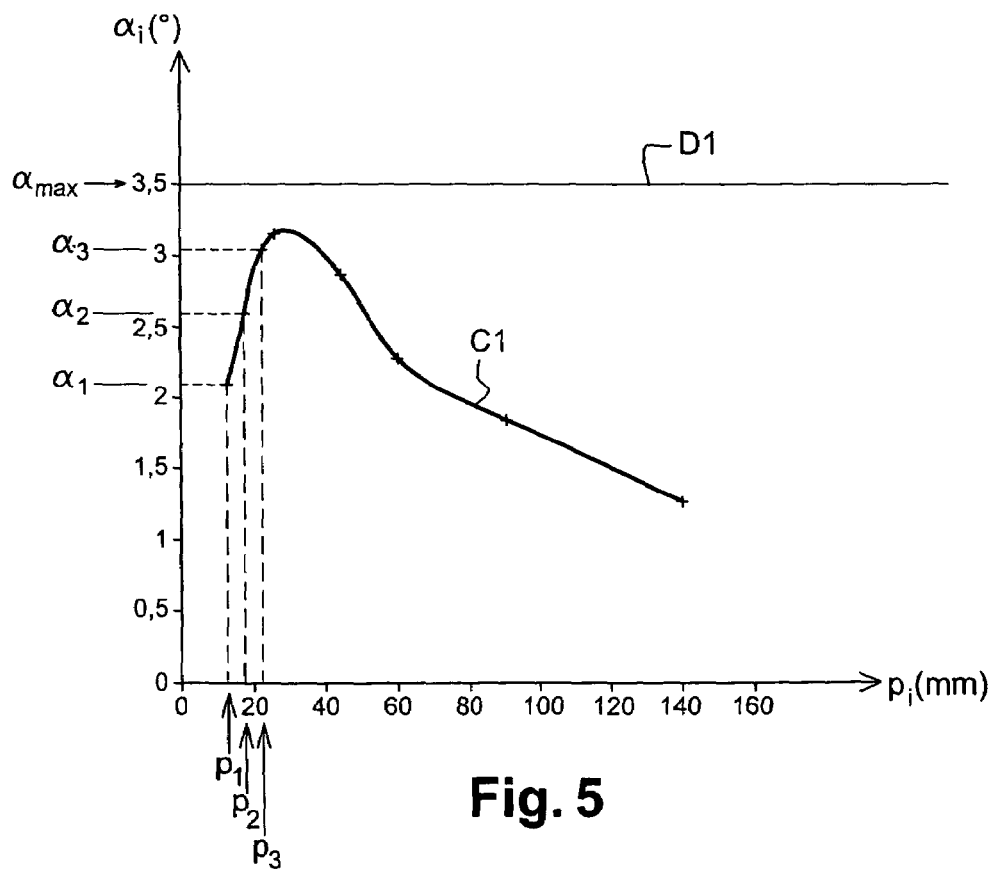
FIG. 5 is a graph showing variation in the angle of inclination of the focused ultrasound beam as a function of the depth of the holes in the calibration parts.

FIG. 5 is a graph showing the curve C1 for variation in the angle of inclination $\alpha_i$ of the axis 38 of the focused beam relative to the normal to the surface of the part plotted as a function of the depth $p_i$ of the flat end of the hole on which the measurement is carried out. This curve is constructed by measuring values for the angle of inclination $\alpha_1$ for the depths $p_1$, $p_2$, and $p_3$, and also for some number of additional steps.

In this example, the calibration parts were made of titanium and the cylindrical flat-ended holes had a diameter of 0.4 mm.

From FIG. 5, it can be seen that the angle of inclination increases from $\alpha_1$ equal to about 2.10°, corresponding to the hole 52 being at a depth $p_1$ of about 15 mm, up to a maximum value equal to about 3.2°, corresponding to a hole at a depth of 31 mm, and thereafter decreases to a value of 1.2° corresponding to a hole at a depth of about 140 mm.

The curve C1 serves to determine the value of the angle of inclination of the axis of the focused beam relative to the normal of the surface of the part beyond which the lateral shadow zone is eliminated over all or nearly all of the depth of the part. This value is given by the maximum value for the angle of inclination $\alpha_i$, as obtained experimentally on the calibration parts.

For a part made of titanium, it thus suffices to tilt the axis of the focused beam on approaching the edges of the part through an angle that is not less than, and that is preferably slightly greater than, 3.2° in order to be able to eliminate the lateral shadow zones.

The method also consists in measuring on a calibration part a value for the angle of inclination of the axis of the focused beam beyond which the amplitude of the wave reflected by a hole begins to decrease from its maximum value when said angle increases.

This value can be determined by using any of the calibration parts that were used for obtaining the plot of curve C1 in FIG. 5.

For a part made of titanium, this value is equal to about 3.5° and is represented in FIG. 5 by a straight line D1.

Thus, in practice, it is possible to tilt the axis of the focused ultrasound beam towards the edge of the part through an angle relative to the normal to the surface of the part, where the angle lies between the maximum value obtained experimentally, i.e. 3.2°, and the value beyond which the amplitude of the wave reflected on the hole begins to decrease, which is 3.5°. This range of values enables the lateral dead zone to be eliminated over the entire depth of the part.

Figure 6:
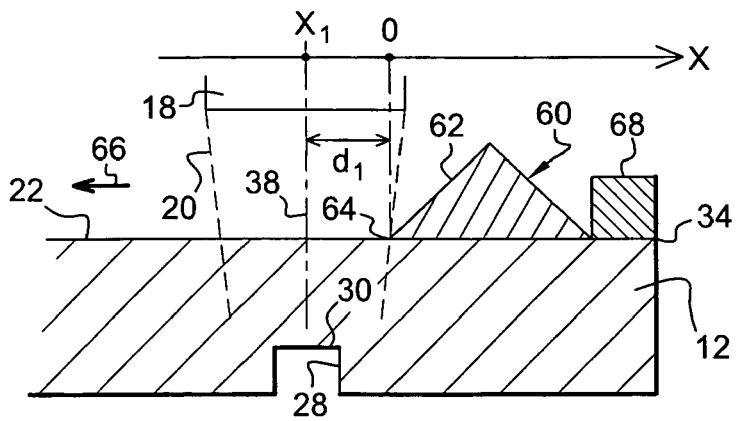
FIGS. 6 and 7 are diagrammatic section views of the part, showing a technique for determining the extent of a lateral shadow zone.
Figure 7:
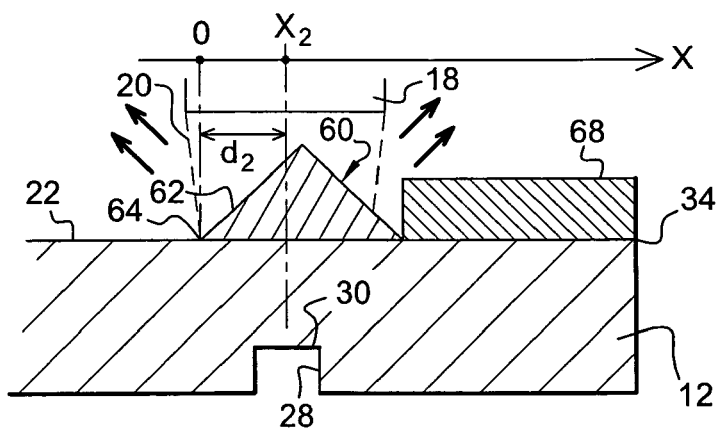

FIGS. 6 and 7 are diagrammatic section views showing a technique for determining the extent of a shadow zone that corresponds to an edge of a part.

The transducer 18 is spaced away from the surface 22 of the part 12 by a water column of predetermined value, and the axis 38 of the focused beam is oriented perpendicularly to the surface 22 of the part and is aligned on a hole 28 having a flat end that is formed in the part at a given depth and at a distance from the edges 34 thereof. The amplitude of the wave reflected on the end wall 30 of the hole is measured and is displayed at 80% of the height of the screen of the means 32.

An element 60 for deflecting the focused beam 20 is placed on the surface 22 of the part and is moved towards the axis 38 of the focused beam 20 in order to deflect a fraction of said focused beam away from the pickup zone of the transducer 18.

In the example shown, the deflection element 60 is a prism having at least one reflection surface 62 that is inclined, e.g. at 45° relative to the surface 22 of the part and to the axis 38 of the focused beam, said face 62 being terminated by an edge 64 in contact with the surface 22 of the part.

The prism 60 is moved stepwise in the direction of arrow 66 along an axis that intersects the axis 38 of the focused ultrasound beam, the prism 60 being moved between two extreme positions in which it is externally tangential to the effective section of the beam focused on the surface 22 of the part, as shown in FIG. 6 where the prism 60 is in the position $X_1$, and in the other of which it deflects the entire focused beam 20, as shown in FIG. 7 where the prism is in the position $X_2$. $d_1$ and $d_2$ are defined as the distances between the axis 38 of the focused beam and the edge 64 of the prism that are equal respectively to $|X_1|$ and $|X_2|$.

By way of example, the prism 60 can be positioned by means of spacers 68 interposed between the prism 60 and the edge 34 of the part, the spacers 68 being of very accurate dimensions and enabling the position of the edge 64 of the prism 60 to be determined with very great precision, e.g. of micrometer order, relative to the axis 38 of the beam.

Figure 8:
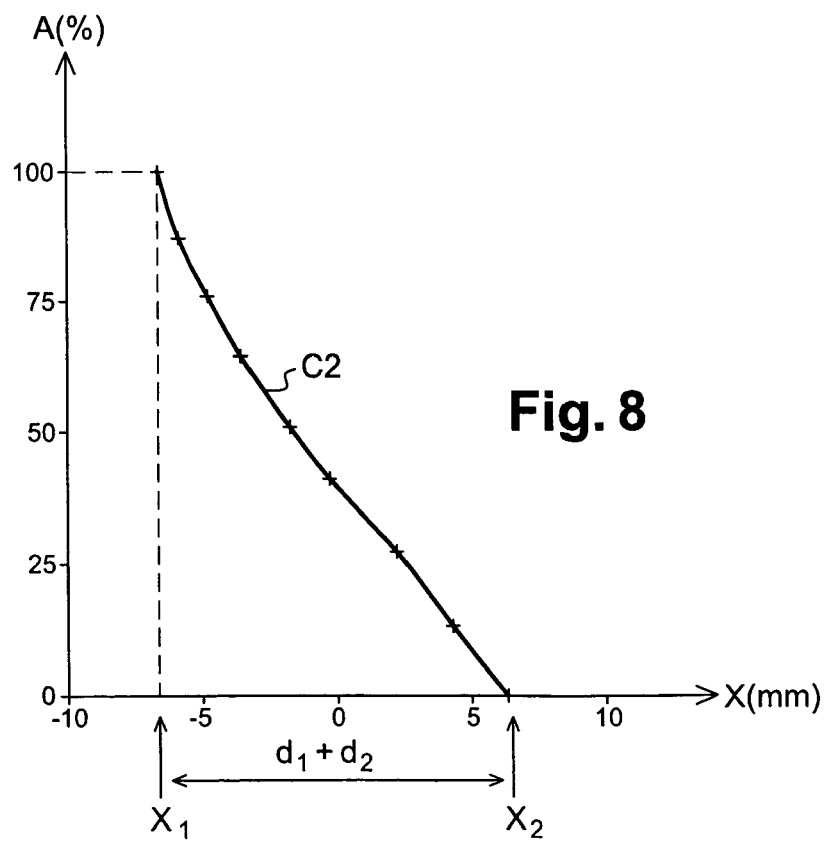
FIG. 8 is a graph showing how the amplitude of an echo of the focused beam varies as a function of the position of an element moved on the surface of the part relative to the beam.

FIG. 8 is a graph showing the curve C2 representing the variation in the amplitude of the echo produced by the focused beam being reflected on the end 30 of the hole as a function of the position 64 of the prism relative to the axis 38 of the focused beam along the axis X. To construct this curve, values are observed for the amplitude of the echo, not only for positions $X_1$ and $X_2$, but also for some number of intermediate positions.

The amplitude decreases from its maximum value corresponding to the position $X_1$ to a value that is zero or substantially zero corresponding to the position $X_2$.

The size of the shadow zone is equal to the radius R of the effective section of the focused beam 20 at the surface of the part, which radius is defined by the expression:

$$R=(d_1+d_1)/2$$

In the example shown in FIG. 8, corresponding to a water column having a value of 40.8 mm between the surface 22 of the part and a Panametric V322-239 440 transducer with a focal length F=8 inches (203.2 mm) and a diameter d=1 inch (25.4 mm), the size of this shadow zone is equal to:

$$R = (d_1 + d_2)/2 = (|X_1| + |X_2|)/2$$
$$= (6.69 \text{ mm} + 6.31 \text{ mm})/2 = 6.50 \text{ mm}$$

In practice, the values of $X_1$, and more particularly of $X_2$, can be difficult to obtain with precision. They can be determined by extrapolation, using appropriate means for calculating linear or polynomial regression on the curve as obtained experimentally.

In a variant, the method may consist in measuring two positions of the edge 64 of the prism that are diametrically opposite about the axis 38 of the focused beam, and in which the edge 64 of the prism is tangential to the effective section of the focused beam 20 at the surface of the part, with the value for the amplitude of the echo produced by the focused beam being reflected on the end of the hole being substantially a maximum value in these two positions.

To do this, the prism 60 is moved on the surface 22 of the part in the direction of arrow 66 to the position $X_1$, and is then placed on the other side of the focused beam 20, symmetrically about the axis 38, and is moved on the surface 22 of the part in the opposite direction to arrow 66 until it reaches a position $X'_1$, equivalent to $X_1$.

The distance between these two positions $X_1$ and $X'_1$ can be used for determining the size of the shadow zone, which is equal to:

$$R=(|X_1|+|X'_1|)/2$$

What is claimed is:

1. A method of inspecting a part in immersion with a multi-element annular ultrasound transducer associated with focusing electronics, the method comprising the steps of:
    emitting a focused ultrasound wave beam;
    picking up echoes produced by the focused ultrasound beam being reflected on a defect in said part, and
    measuring an amplitude of said echoes,
    wherein, when an axis of the focused beam is remote from an edge of the part, the step of emitting is performed so that the axis of the emitted focused ultrasound beam is perpendicular to a surface of the part, and
    wherein, when the axis of the focused ultrasound beam is close to an edge of the part so as to pass into a shadow zone associated with said edge, the step of emitting is performed so that the axis of the emitted focused ultrasound beam is tilted towards the edge of the part relative to the normal to the surface of the part, by an angle that is small enough to avoid modifying the amplitude of the echoes relative to the amplitude measured when said focused ultrasound beam is emitted perpendicularly to the surface of the part, and large enough to eliminate the shadow zone over all or substantially all of a depth of the part.

2. A method according to claim 1, comprising initially a step of using calibration parts to measure first values for said angle beyond which the shadow zone is eliminated at different depths within the part, and a step of selecting for inspection purposes an angle that is not less than, or that is slightly greater than, the maximum of said first measured values.

3. A method according to claim 2, further comprising measuring on a calibration part a second value for the angle of inclination beyond which the amplitude of the echoes from a calibrated defect begins to decrease with increasing angle, and selecting for inspection purposes an angle of inclination for the axis of the focused ultrasound beam that lies between the maximum of said first values and said second value.

4. A method according to claim 1, wherein the angle of inclination of the incident focused beam relative to the normal to the surface of the part is about 3°.

5. A method according to claim 1, further comprising determining an extent of the shadow zone comprises:
    moving a deflector element for deflecting the focused ultrasound beam in translation on the surface of the part along an axis intersecting the axis of the focused ultrasound beam; and
    identifying positions of said deflector element at which the amplitude of the echo produced by the reflection of the focused ultrasound beam on the defect varies between a maximum value and a minimum value.

6. A method according to claim 5, wherein the deflector element is a prism presenting at least one reflection face that is inclined to the surface of the part and to the axis of the focused beam.

7. A method according to claim 6, further comprising:
    identifying two diametrically opposite positions of the prism about the axis of the focused ultrasound beam for which the amplitude of the echo produced by the focused ultrasound beam reflected on the defect begins to decrease from a maximum value as the prism approaches the axis of the focused ultrasound beam; and
    calculating half the distance between said two diametrically opposite positions in order to obtain the extent of the shadow zone.

8. A method according to claim 1, wherein said shadow zone is a region of said part in which at least a part of said focused ultrasound beam passes beyond said edge of said part and is not reflected by said defect.

* * * * *